United States Patent [19]

Hölter et al.

[11] Patent Number: 4,875,406
[45] Date of Patent: Oct. 24, 1989

[54] DEVICE FOR DETECTING DIFFERENT POLLUTANTS IN GAS STREAMS

[75] Inventors: Heinz Hölter, Beisenstrasse 39–41, 4390 Gladbeck; Heinrich Igelbüscher, Gladbeck; Heinrich Gresch, Dortmund-Wickede; Heribert Dewert, Gladbeck; Peter Burggräf, Bochum, all of Fed. Rep. of Germany

[73] Assignee: Heinz Hölter, Gladbeck, Fed. Rep. of Germany

[21] Appl. No.: 177,549

[22] PCT Filed: Jul. 29, 1987

[86] PCT No.: PCT/EP87/00411
§ 371 Date: Mar. 25, 1988
§ 102(e) Date: Mar. 25, 1988

[87] PCT Pub. No.: WO88/01057
PCT Pub. Date: Feb. 11, 1988

[30] Foreign Application Priority Data

Aug. 2, 1986 [DE] Fed. Rep. of Germany ....... 3626277
Nov. 28, 1986 [DE] Fed. Rep. of Germany ....... 3640734

[51] Int. Cl.$^4$ .............................................. B60H 1/28
[52] U.S. Cl. ....................................... 98/2.01; 98/2.16
[58] Field of Search ....................... 98/2.01, 2.11, 2.16, 98/2.17

[56] References Cited

U.S. PATENT DOCUMENTS 3,041,591  6/1962  Moore ................................. 340/237
4,478,049  10/1984  Fukui et al. ..................... 98/2.01 X

FOREIGN PATENT DOCUMENTS 42287    12/1981  European Pat. Off. .
53394     6/1982  European Pat. Off. ............. 98/2.01
3304324   8/1984  Fed. Rep. of Germany .
58-191622 11/1983 Japan ................................. 98/2.01
59-48216   3/1984 Japan ................................. 98/2.01

Primary Examiner—Harold Joyce
Attorney, Agent, or Firm—Herbert Dubno

[57] ABSTRACT

A device for the detection of various pollutant contents in gas streams, preferably in the supply to motor vehicle cabins or protection cabins for operators, with use of one or several pollutant-detecting semiconductor gas sensors. A gas sensor (4) is alternately exposed to the gas streams to be evaluated. The sensor is placed at the separation point between the outer air and the cabin air, whereby, through switching which is effected within seconds, a practially constant comparison between the quality of the inner air and the outer air is performed. For this purpose, a switching arrangement is assigned to the gas sensor (4). The gas sensor (4) and the switching arrangement can be mounted on the fresh air/ambient air valve (3). The output signal of the gas sensor (4) serves for the control of the fresh air/ambient air valve (3).

4 Claims, 2 Drawing Sheets

DEVICE FOR DETECTING DIFFERENT POLLUTANTS IN GAS STREAMS

The invention relates to a device for the detection of different pollutants in gas streams, preferably for feeding to the cabins of motor vehicles or to protection cabins for operators, involving the use of one or more pollutant-detecting semiconductor gas sensors.

BACKGROUND OF THE INVENTION

It is known to use pollutant-detecting gas sensors for the control of fresh air/ambient air valves. These sensors additionally may be employed for switching on- and off filter devices in motor vehicle cabins and protection cabins for equipment operators. Furthermore, it is known that these semiconductor gas sensors, due to their measuring mode and manufacture, have tolerances too high for this type of application.

A great number of proposals have been made to improve the sensitivity and stability of these sensors. These have, however, not been successful. For instance, when the pollutant-detecting gas sensors are used in motor vehicles, the transverse sensitivity towards various travel speeds, temperatures, degrees of humidity and so on, is still unacceptably high.

In order to eliminate these disadvantages, the invention proposes that a gas sensor should be exposed alternately to the gas streams to be evaluated. The sensor is mounted at the separation point between the outside air and the cabin air. Thereby through switching, effected within seconds, practically a constant comparison between the quality of the inner air and the outer air is established. For this purpose, the gas sensor cooperates with a switching device. The gas sensor and the switching device can be arranged on a fresh air/ambient air valve. The output signals of the gas sensor serve for controlling the fresh air/ambient air valve.

It is known that semiconductor sensors, particularly of the stannic dioxide variety, have a very high transverse sensitivity towards temperature- and humidity variations such as in the degree of humidity. Sometimes the variations are so high that they can lead to deviations up to 70% in the measured value, namely due to various humidity degrees. The influence of temperature variations can have similar effects. It is known to create a temperature compensation by means of temperature sensors. Humidity can be technically measured only as relative humidity. This measured value, however, leads to very different absolute humidities at various air temperatures. Measurement of the realtive humidity thus cannot be directly used for the correction of the humidity flow. As a result, the correction becomes very complicated and can be generally figured out only by a computer.

SUMMARY OF THE INVENTION

In order to be capable to perform especially a correction of temperature- and humidity variations in a gas stream, the invention proposes that the measured value established by a semiconductor sensor be corrected by a microprocessor-originated correction factor, determined by an average value of temperature and humidity. The temperature- and humidity values are set in a two-dimensional matrix, so that in a microprocessor of only 4 K capacity a field with 200 values can be stored, which is sufficiently adequate to carry out a quite accurate compensation.

BRIEF DESCRIPTION OF THE DRAWING

Specific embodiments of the invention are now detailed with the aid of the drawing, which shows.

DETAILED DESCRIPTION

Figure 1:
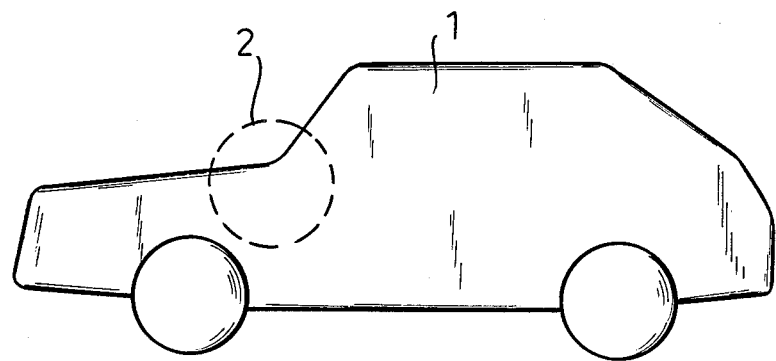
FIG. 1 is a schematic representation of a motor vehicle which can be equipped with a device for detecting various pollutants in a gas stream according to the invention.
Figures 1A, 1B:
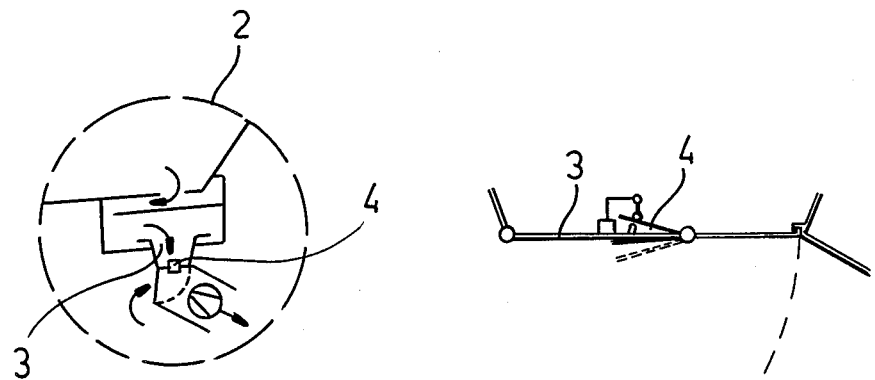
FIG. 1A is a detail of the region in which the gas sensor is placed in the vehicle of FIG. 1.
FIG. 1B is a view of a portion of FIG. 1A drawn to a larger scale showing the location of the gas sensor with its switching device on the air valve flap.

FIG. 1 illustrates a motor vehicle 1 and the air supply area 2 for the motor vehicle. The pollutant-detecting gas sensor 4 is placed at the separation point between the outer air and the cabin air, being provided with a switching device. Gas sensor 4 with its switching device can be arranged on the ambient-air valve 3 as will be apparent from FIGS. 1A and 1B.

Due to this configuration, it is insured that the sensor mounted at a stationary measuring point for detecting the absolute values of pollutant, no longer requires an enormous checking and setting effort. Moreover the possibility now exists to use simple sensors, which can safely evaluate the difference between better or more polluted air and, in the end, give the output signal for the control of the fresh air/ambient air valve.

The basic concept of this embodiment consists thus in bringing about the continuously running comparison between the quality of two air streams, by means of a pollutant-detecting gas sensor with the assistance of a mechanical switching device.

Figure 2:
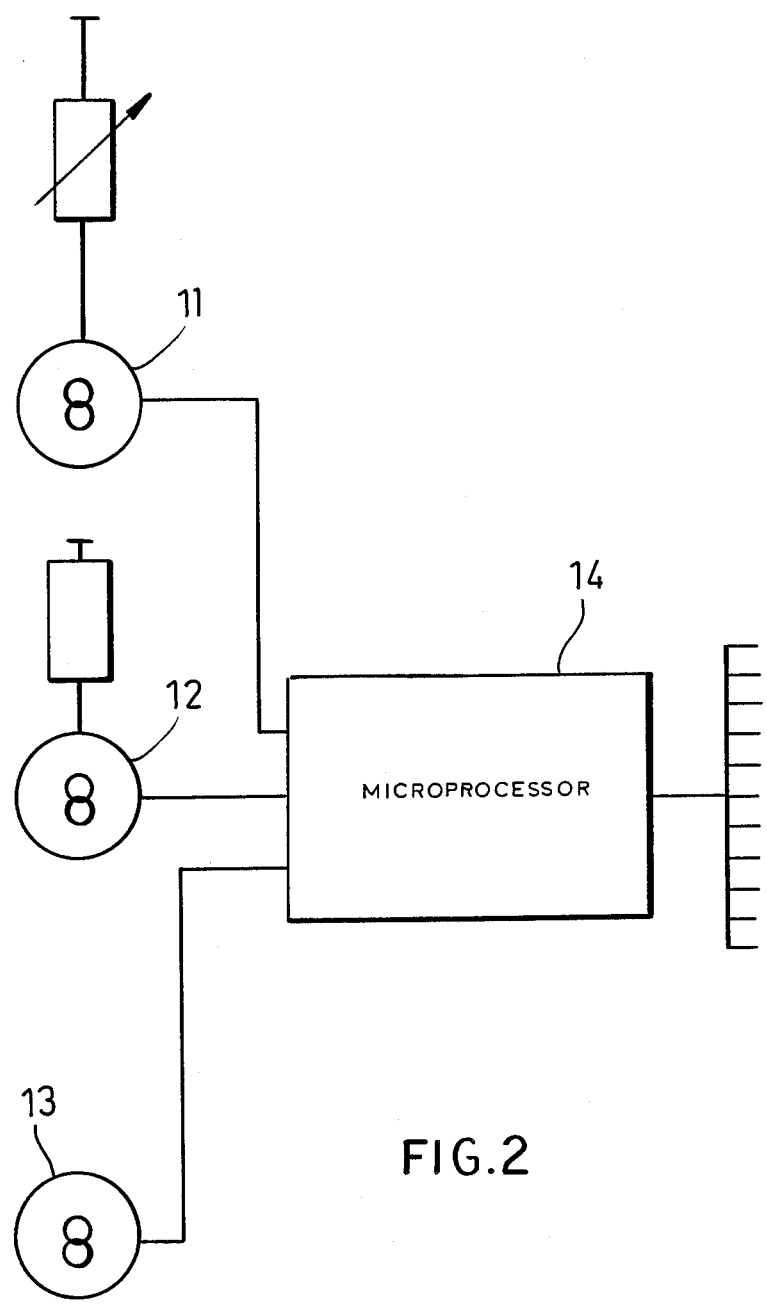
FIG. 2 is a circuit diagram in block form of a switching arrangement for correcting the temperature and humidity oscillations in a gas stream.

In the embodiment of FIG. 2 there is schematically illustrated a gas sensor 11, temperature sensor 12, and humidity sensor 13. The three sensors 11, 12, 13 transmit their values in common to the microprocessor 14.

The microprocessor 14 seeks for the temperature- and humidity values each time the corresponding correction value, which corrects the gas sensor value.

This way, a heat- and humidity-independent output signal is obtained.

We claim:

1. A device for the detection of various pollutants in a gas stream supplied to motor vehicle cabins or operator protection cabins comprising:
   at least one semiconductor gas sensor;
   a means for alternately exposing said gas stream to be evaluated to said sensor; and
   a microprocessor functioning to correct, with the aid of a correction factor, pollutant values measured by said semiconductor gas sensor, said correction factor being related to an average value of temperature and humidity.

2. A device according to claim 1 wherein said means for alternately exposing said gas stream is a switching device.

3. A device according to claim 2 wherein said gas sensor and said switching device are mounted on a fresh air/ambient air valve.

4. A device according to claim 3 wherein an output signal of said gas sensor serves for controlling the fresh air/ambient air valve.

* * * * *